(12) United States Patent
Leibowitz

(10) Patent No.: US 11,517,370 B2
(45) Date of Patent: Dec. 6, 2022

(54) SURGICAL FORCEPS HAVING A CUTTING EDGE

(71) Applicant: COVIDIEN LP, Mansfield, MA (US)

(72) Inventor: Dalia P. Leibowitz, Cambridge, MA (US)

(73) Assignee: COVIDIEN LP, Mansfield, MA (US)

( * ) Notice: Subject to any disclaimer, the term of this patent is extended or adjusted under 35 U.S.C. 154(b) by 769 days.

(21) Appl. No.: 16/503,672

(22) Filed: Jul. 5, 2019

(65) Prior Publication Data

US 2021/0000534 A1 Jan. 7, 2021

(51) Int. Cl.
*A61B 18/12* (2006.01)
*A61B 18/14* (2006.01)
A61B 18/00 (2006.01)
A61B 34/35 (2016.01)

(52) U.S. Cl.
CPC ...... *A61B 18/1445* (2013.01); *A61B 18/1206* (2013.01); *A61B 34/35* (2016.02); *A61B 2018/0063* (2013.01); *A61B 2018/00178* (2013.01); *A61B 2018/00297* (2013.01); *A61B 2018/00589* (2013.01); *A61B 2018/00595* (2013.01); *A61B 2018/00601* (2013.01); *A61B 2018/146* (2013.01); *A61B 2018/1412* (2013.01); *A61B 2018/1457* (2013.01)

(58) Field of Classification Search
CPC ............ A61B 18/1206; A61B 18/1445; A61B 2018/1457; A61B 2018/146
See application file for complete search history.

(56) References Cited

U.S. PATENT DOCUMENTS

| | | | |
|---|---|---|---|
| 6,358,268 B1 | 3/2002 | Hunt et al. | |
| 8,197,472 B2 | 6/2012 | Lau et al. | |
| 8,663,222 B2* | 3/2014 | Anderson | A61B 18/1206 606/52 |
| 8,968,305 B2 | 3/2015 | Dumbauld et al. | |
| 9,492,221 B2 | 11/2016 | Garrison | |
| 2011/0112569 A1* | 5/2011 | Friedman | A61B 5/283 600/509 |
| 2013/0103030 A1* | 4/2013 | Garrison | A61B 18/1442 606/45 |
| 2016/0074098 A1* | 3/2016 | Kappus | A61B 18/1445 606/41 |

\* cited by examiner

*Primary Examiner* — Daniel W Fowler
(74) *Attorney, Agent, or Firm* — Carter, DeLuca & Farrell LLP

(57) ABSTRACT

A surgical forceps includes an end effector assembly including a first jaw member and a second jaw member pivotally engaged with one another. At least one of the first or second jaw member is pivotable between a spaced-apart position and an approximated position. The first jaw member includes first and second surfaces on opposite sides thereof. The first surface is disposed in opposition to the second jaw member. The second surface includes a cutting edge disposed on a proximal portion thereof. The second jaw member includes a proximal flange having first and second raised sidewalls defining a proximal channel therebetween. The proximal channel receives the cutting edge of the first jaw member when the first and second jaw members are in the approximated position. The cutting edge of the first jaw member is exposed when the first and second jaw members are in the spaced apart position.

10 Claims, 6 Drawing Sheets

SURGICAL FORCEPS HAVING A CUTTING EDGE

BACKGROUND

Technical Field

The present disclosure relates to surgical instruments and, more particularly, to surgical forceps for grasping, sealing and/or dividing tissue having a cutting edge.

Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue seal.

During minimally invasive surgical procedures, such as laparoscopic procedures, surgical forceps may be used for forming or expanding an operative hole. The operative hole may be formed before a surgical procedure begins. The operative hole may be expanded in diameter after the surgical procedure has begun or when a surgical procedure is nearing completion. As an example, an outer surface of surgical forceps may be used for creating or expanding an operative hole to a desired size or diameter. Thus, desired surgical instruments pass through the hole for performing operative procedures. The operative hole also may also be used for extracting treatment tissue or removing an organ.

SUMMARY

In accordance with an aspect of the present disclosure, a surgical forceps includes an end effector assembly. The end effector assembly includes a first jaw member and a second jaw member pivotally engaged with one another. At least one of the first or second jaw member is pivotable relative to the other of the first or second jaw member between a spaced-apart position and an approximated position. The first jaw member includes first and second surfaces on opposite sides thereof. The first surface is disposed in opposition to the second jaw member. The second surface includes a cutting edge disposed on a proximal portion thereof facing away from the second jaw member. The second jaw member includes a proximal flange having first and second raised sidewalls defining a proximal channel therebetween. The proximal channel receives the cutting edge of the first jaw member therebetween when the first and second jaw members are disposed in the approximated position. The cutting edge of the first jaw member is exposed when the first and second jaw members are disposed in the spaced apart position.

In some aspects, the proximal portion of the first jaw member including the cutting edge includes a height greater than a height of a distal portion of the first jaw member.

In some aspects, a pivot pin is engaged with the first and second raised sidewalls of the proximal flange of the second jaw member to pivotally engage the first and second jaw members with one another.

In some aspects, a distal end of the proximal channel is open.

In some aspects, the cutting edge includes a sharp tip at a distal end thereof configured to cut tissue.

BRIEF DESCRIPTION OF THE DRAWINGS

The accompanying drawings, which are incorporated in and constitute a part of this specification, illustrate embodiments of the present disclosure and, together with the detailed description below, serve to further explain the present disclosure, in which.

DETAILED DESCRIPTION

Figure 1:
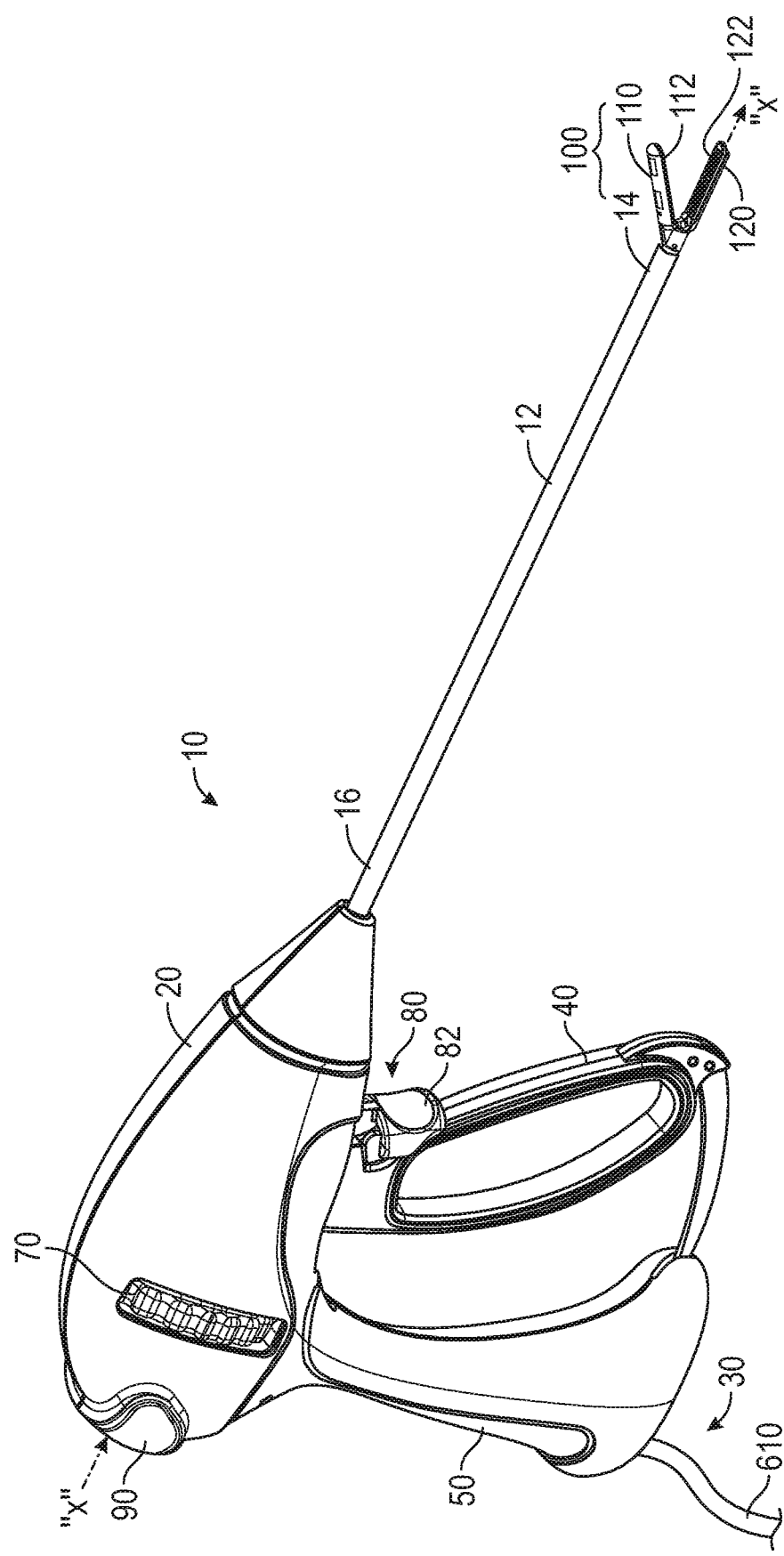
FIG. 1 is a front, perspective view of an endoscopic surgical forceps configured for use in accordance with the present disclosure.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

"About" or "approximately" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the present disclosure should typically be considered as available and applicable to other similar features or aspects in another exemplary embodiment of the present disclosure. Accordingly, technical features described herein according to one exemplary embodiment of the present disclosure may be applicable to other exemplary embodiments of the present disclosure, and thus duplicative descriptions may be omitted herein.

Exemplary embodiments of the present disclosure will be described more fully below (e.g., with reference to the accompanying drawings). Like reference numerals may refer to like elements throughout the specification and drawings.

Figure 2:
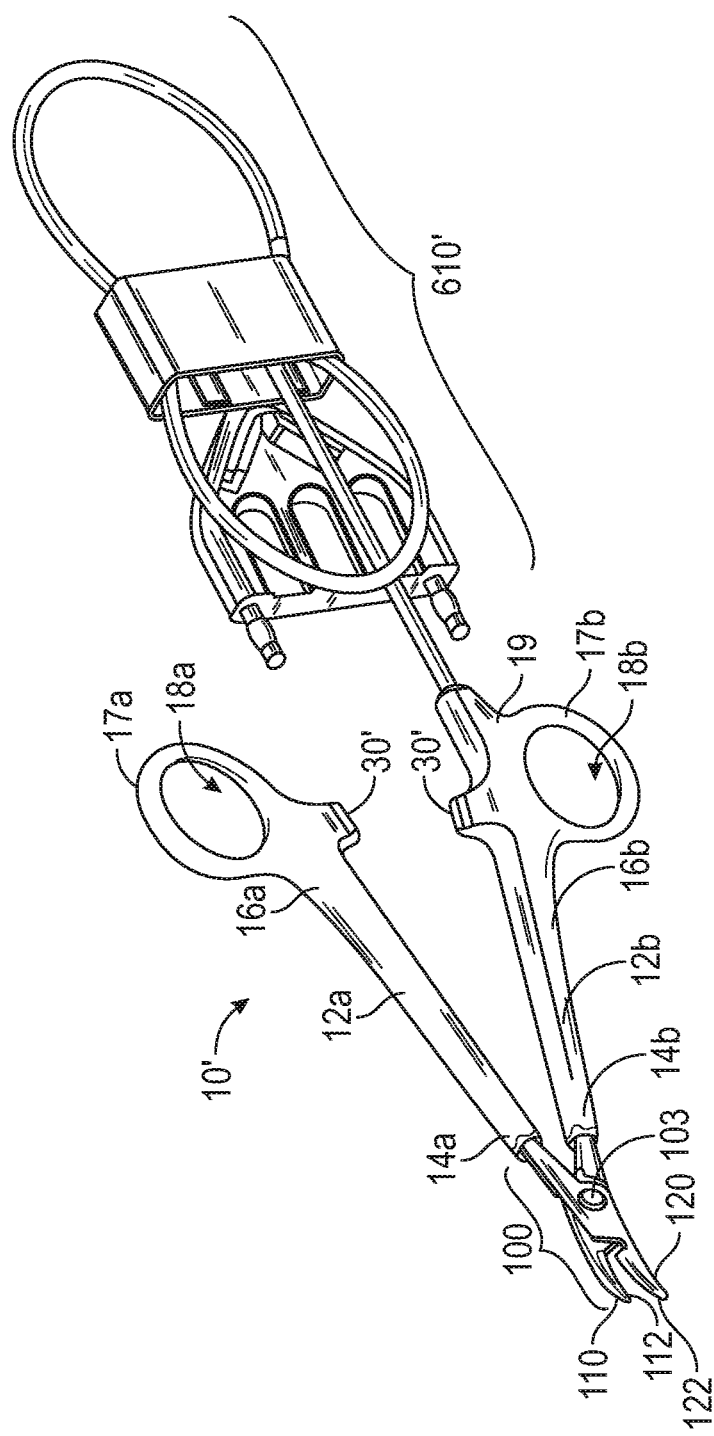
FIG. 2 is a front, perspective view of an open surgical forceps configured for use in accordance with the present disclosure.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic instrument, e.g., forceps 10, or an open instrument, e.g., forceps 10', may be utilized in accordance with the present disclosure. Obviously, different electrical and mechanical connections and considerations apply to each particular type of instrument, however, the novel aspects with respect to the end effector assembly and its operating characteristics remain generally consistent with respect to both the open and endoscopic configurations.

Turning now to FIG. 1, an endoscopic forceps 10 is provided defining a longitudinal axis "X-X" and including a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source, although forceps 10 may alternatively be configured as a battery powered instrument. Cable 610 includes a wire (or wires) (not shown) extending therethrough that has sufficient length to extend through shaft 12 in order to provide electrical energy to at least one of the sealing plates 112, 122 of jaw members 110, 120, respectively, of end effector assembly 100, e.g., upon activation of activation switch 90.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about longitudinal axis "X-X" to rotate end effector 100 about longitudinal axis "X-X." Housing 20 houses the internal working components of forceps 10.

End effector assembly 100 is shown attached at a distal end 14 of shaft 12 and includes a pair of opposing jaw members 110 and 120. Each of the jaw members 110 and 120 includes an opposed electrically-conductive tissue sealing plate 112, 122, respectively. End effector assembly 100 is designed as a unilateral assembly, i.e., where jaw member 120 is fixed relative to shaft 12 and jaw member 110 is moveable relative to shaft 12 and fixed jaw member 120. However, end effector assembly 100 may alternatively be configured as a bilateral assembly, i.e., where both jaw member 110 and jaw member 120 are moveable relative to one another and to shaft 12. In some embodiments, a knife assembly is disposed within shaft 12 and a knife channel (e.g., 125—see, e.g., FIGS. 3 and 4) is defined within one or both jaw members 110, 120 to permit reciprocation of a knife therethrough, e.g., via activation of a trigger 82 of trigger assembly 80. In some embodiments, reciprocation of the knife may be optionally performed after tissue sealing. The particular features of end effector assembly 100 will be described in greater detail hereinbelow.

Continuing with reference to FIG. 1, moveable handle 40 of handle assembly 30 is ultimately connected to a drive assembly (not shown) that, together, mechanically cooperate to impart movement of jaw members 110 and 120 between a spaced-apart position and an approximated position to grasp tissue disposed between sealing plates 112 and 122 of jaw members 110, 120, respectively. As shown in FIG. 1, moveable handle 40 is initially spaced-apart from fixed handle 50 and, correspondingly, jaw members 110, 120 are in the spaced-apart position.

Referring now to FIG. 2, an open forceps 10' is shown including two elongated shafts 12a and 12b, each having a proximal end 16a and 16b, and a distal end 14a and 14b, respectively. Similar to forceps 10 (FIG. 1), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably coupled to one another. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another which, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30' may be included for selectively locking the jaw members 110 and 120 relative to one another at various positions during pivoting. Ratchet 30' may include graduations or other visual markings that enable the user to easily and quickly ascertain and control the amount of closure force desired between the jaw members 110 and 120.

With continued reference to FIG. 2, one of the shafts, e.g., shaft 12b, includes a proximal shaft connector 19 that is designed to connect the forceps 10' to a source of electrosurgical energy such as an electrosurgical generator (not shown). Proximal shaft connector 19 secures an electrosurgical cable 610' to forceps 10' such that the user may selectively apply electro surgical energy to the electrically-conductive tissue sealing plates 112 and 122 of jaw members 110 and 120, respectively, as needed.

Figure 3:
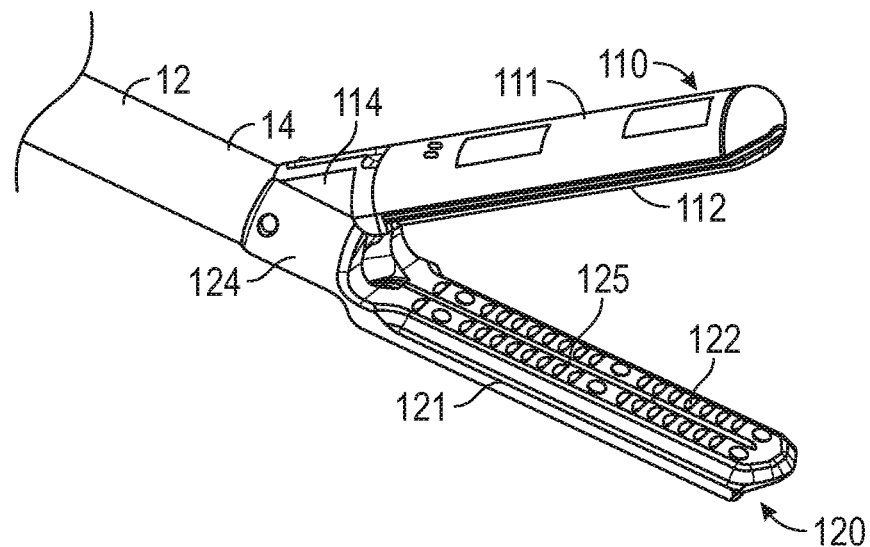
FIG. 3 is an enlarged, front, perspective view of an end effector assembly configured for use with the forceps of FIGS. 1 and 2.

Turning now to FIG. 3, end effector assembly 100, including jaw members 110 and 120 is configured for use with either forceps 10 or forceps 10', discussed above, or any other suitable surgical instrument capable of pivoting jaw members 110, 120 relative to one another between a spaced-apart position and an approximated position for grasping tissue therebetween. However, for purposes of simplicity and consistency, end effector assembly 100 will be described hereinbelow with reference to forceps 10 only.

Jaw members 110, 120, as shown in FIG. 3, each include an outer jaw housing 111, 121 and an electrically-conductive tissue sealing plate 112, 122 disposed atop respective jaw housings 111,121. A proximal flange 114,124 extends proximally from each of jaw housings 111, 121, respectively, for pivotably coupling jaw members 110, 120 to one another. Further, proximal flange 124 of jaw member 120 engages jaw member 120 to shaft 12. Alternatively, in embodiments where end effector assembly 100 is configured as a bilateral assembly, jaw member 120 is only coupled to jaw member 110 via proximal flange 124 and is not engaged to shaft 12 such that both jaw members 110, 120 may be pivoted relative to one another and to shaft 12 between the spaced-apart and approximated positions. Jaw housings 111, 121 of jaw members 110, 120, respectively, may be formed from stainless steel, or any other suitable material, e.g., electrically-insulative materials. Proximal flanges 114, 124 of jaw members 110, 120 define a bifurcated configuration, as will be described in greater detail below, and may be formed with jaw housings 111, 121, respectively, via molding or via any other suitable manufacturing process, e.g., machining, stamping, forging, or casting. In unilateral embodiments, proximal flange 124 of jaw member 120 may also be molded or otherwise engaged to shaft 12.

Electrically-conductive tissue sealing plates 112, 122 of jaw members 110, 120, respectively, each define an exposed tissue-sealing surface that opposes the tissue sealing surface defined by the sealing plate 112, 122 of the other jaw member 110, 120. Tissue sealing plates 112, 122 of jaw members 110, 120, respectively, are adapted to connect to a source of energy (not explicitly shown), thus functioning as electrodes for conducting energy therebetween and through tissue to treat tissue.

Proximal flanges 114, 124 of jaw members 110, 120, respectively, are formed from electrically-insulative materials, e.g., plastic, to inhibit shorting of tissue sealing plates 112, 122 during tissue treatment. Alternatively, proximal flanges 114, 124 may be formed from stainless steel, or other conductive materials so long as flanges 114, 124 are isolated from tissue sealing plates 112, 122. More specifically, since flanges 114, 124 of jaw members 110, 120, respectively, are pivotably coupled to one another, e.g., to permit movement of jaw members 110, 120 relative to one another between the spaced-apart and approximated positions, forming flanges 114, 124 from electrically-insulative materials (or isolating flanges 114, 124) inhibits direct electrical contact between tissue sealing plates 112, 122 of jaw members 110, 120, respectively, thus inhibiting shorting and/or damage to surrounding tissue. Forming proximal flanges 114, 124 from plastic, for example, also allows for relatively inexpensive manufacture, as the molding process is a relatively inexpensive process for forming proximal flanges 114, 124 with complex features to facilitate the pivotable coupling therebetween. The specific configurations and features of proximal flanges 114, 124 of jaw members 110, 120, respectively, will be described in greater detail below. Shaft 12 may likewise be formed from a plastic (or other suitable material) and, in unilateral embodiments, as mentioned above, may be molded with proximal flange 124 of jaw member 120 to form a single component. Forming shaft 12 from an electrically-insulative material, e.g., plastic, (or insolating shaft 12 from tissue sealing plates 112, 122, where shaft 12 is formed from a conductive material) also helps to maintain the electrical isolation between tissue sealing plates 112, 122 of jaw members 110, 120, respectively, thus inhibiting shorting of tissue sealing plates 112, 122 and/or damage to surrounding tissue, although other configurations are also contemplated.

Figure 4:
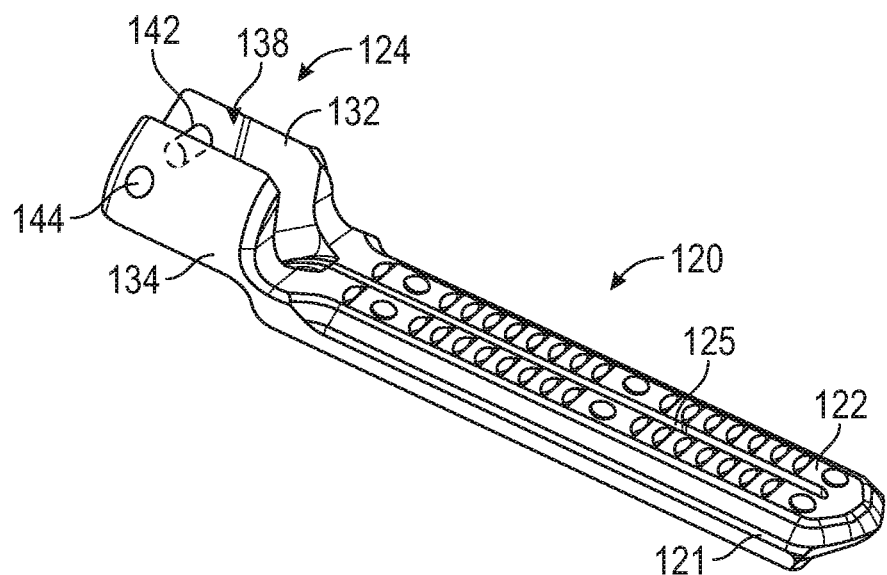
FIG. 4 is an enlarged, front, perspective view of one of the jaw members of the end effector assembly of FIG. 3.

With reference to FIG. 4, jaw member 120 includes, as mentioned above, outer jaw housing 121, electrically-conductive tissue sealing plate 122 disposed atop outer jaw housing 121, and proximal flange 124 extending proximally from outer jaw housing 121 and configured to pivotably couple to proximal flange 114 of jaw member 110 (see FIG. 3). More specifically, proximal flange 124 defines a generally U-shaped, bifurcated configuration including first and second spaced-apart flange components 132, 134 that are interconnected by a base 136. Flange components 132, 134 define a channel 138 extending longitudinally therebetween that, as will be described below, is configured to receive at least a portion of proximal flange 114 of jaw member 110 (see FIG. 3) for pivotably coupling jaw members 110, 120 (FIG. 3) to one another and to permit moving jaw members 110, 120 (FIG. 3) between the spaced-apart and approximated positions.

Continuing with reference to FIG. 4, flange component 132 of proximal flange 124 of jaw member 120 includes a generally cylindrically-shaped protrusion 142 extending outwardly therefrom. Protrusion 142 may be monolithically formed with proximal flange 124 during the molding process, or any other suitable manufacturing process used, e.g., machining, stamping, forging, or casting. Flange component 134, on the other hand, defines an aperture 144 extending transversely therethrough that is substantially aligned with protrusion 142. Aperture 144 may be formed within flange component 134 during the manufacturing process, e.g., the molding process. Forming protrusion 142 on flange component 132 and defining aperture 144 through flange component 134 via the molding process is advantageous in that precise alignment of protrusion 142 and aperture 144 relative to one another can be achieved relatively easily. Alternatively, as described in more detail below with reference to FIGS. 5-9, a pivot pin 601 may engage apertures (see, e.g., aperture 144) on flange components 132 and 134 to secure the flange components of jaw member 120 to jaw member 110. Thus, jaw member 120 is pivotally coupled with jaw member 120 by pivot pin 601.

Figure 5:
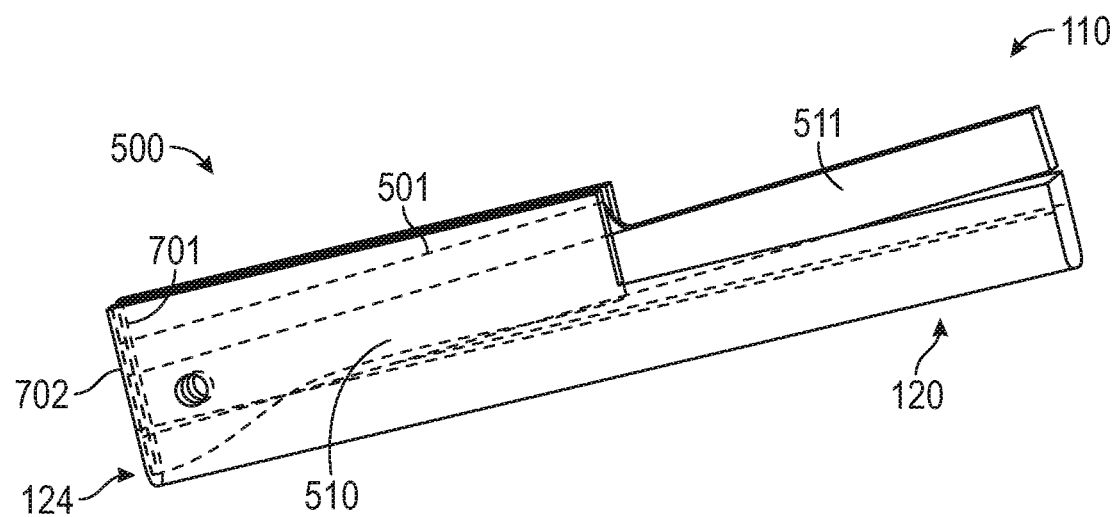
FIG. 5 is an enlarged, side view of a first jaw member having a proximal cutting edge engaged between raised sidewalls of a second jaw member in accordance with the present disclosure.
Figure 6:
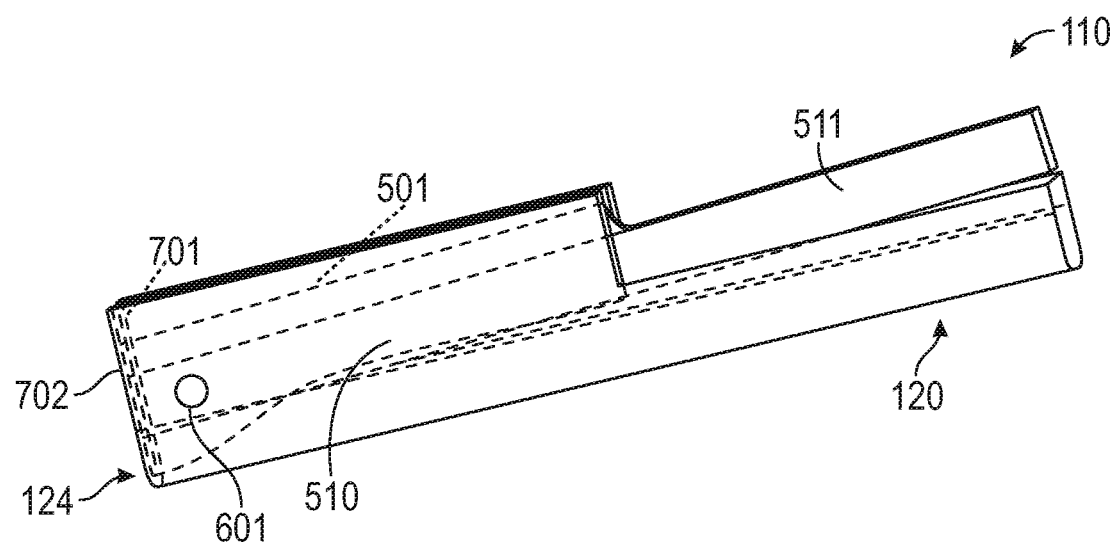
FIG. 6 is an enlarged, side view of a first jaw member pivotally coupled to a second jaw member by a pivot pint, the first jaw member having a proximal cutting edge engaged between raised sidewalls of the second jaw member in accordance with the present disclosure.
Figure 7:
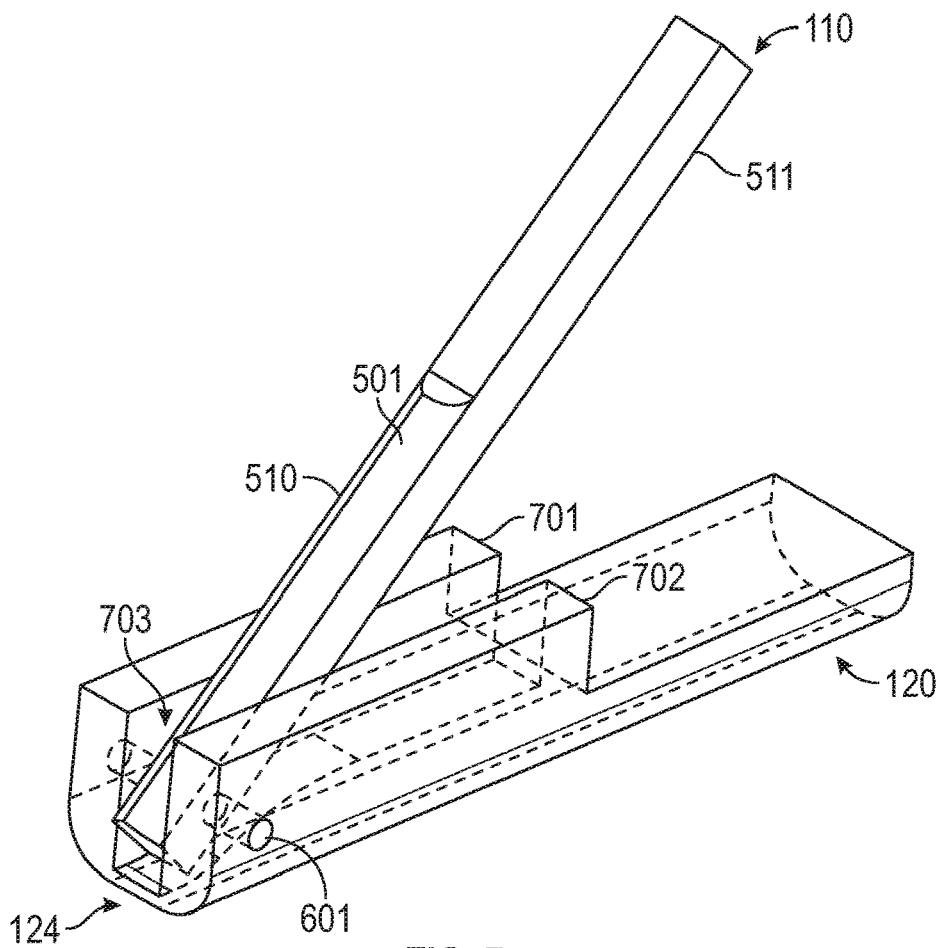
FIG. 7 is an enlarged perspective view of a first jaw member having a proximal cutting edge exposed with respect to raised sidewalls of a second jaw member and with respect to a proximal channel of the second jaw member in accordance with the present disclosure.
Figure 8:
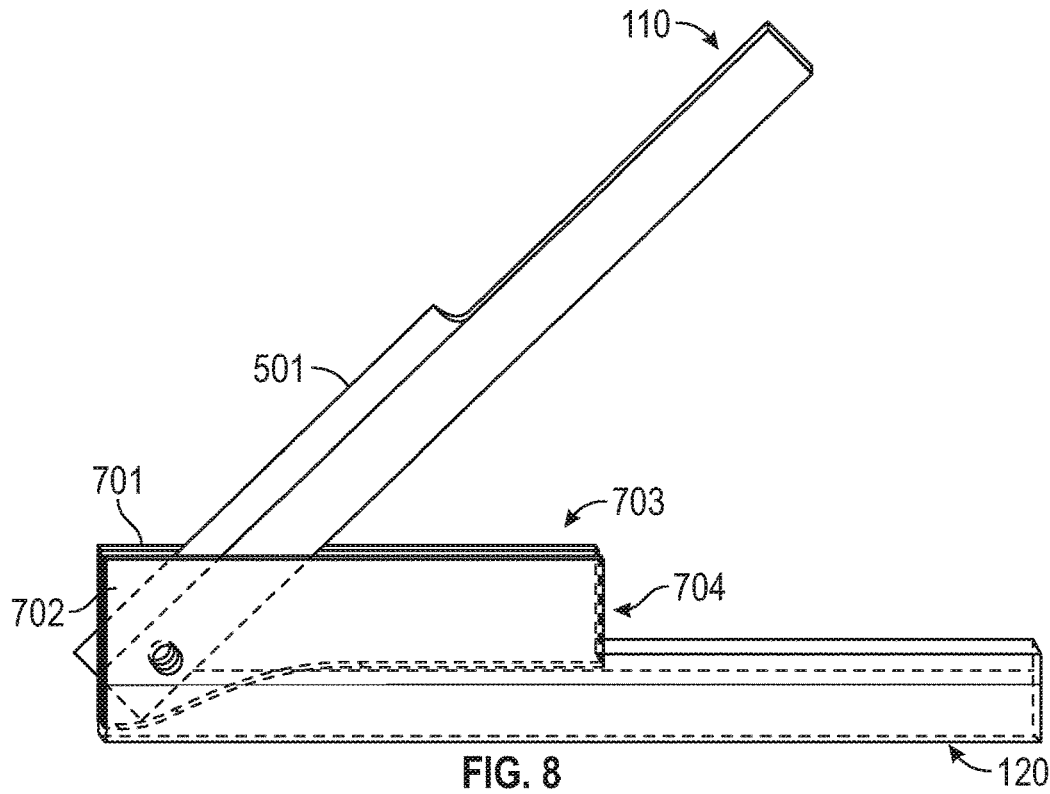
FIG. 8 is an enlarged, side view of a first jaw member having a proximal cutting edge exposed with respect to raised sidewalls of a second jaw member and with respect to a proximal channel of the second jaw member in accordance with the present disclosure.
Figure 9:
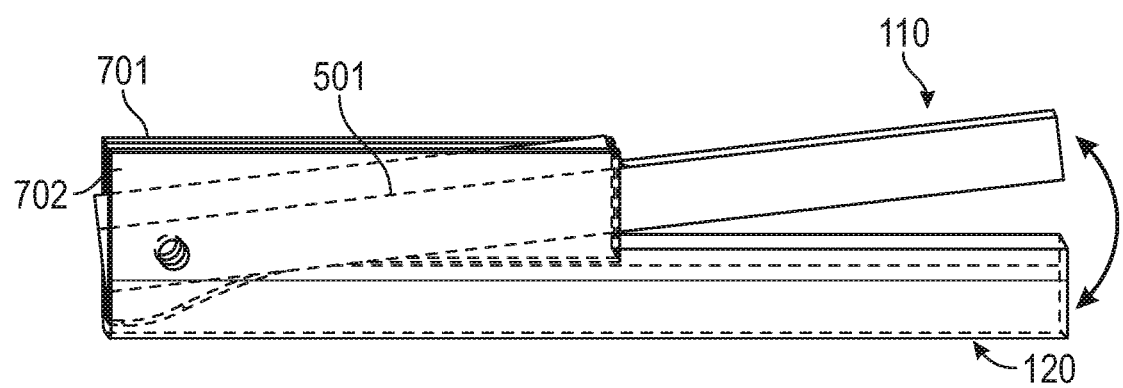
FIG. 9 is an enlarged, side view of pivoting directions of a first jaw member having a proximal cutting edge with respect to raised sidewalls of a second jaw member and with respect to a proximal channel of the second jaw member in accordance with the present disclosure.

Referring to FIGS. 5-9, according to aspects of the present disclosure, a surgical forceps includes an end effector assembly 500. The end effector assembly 500 includes a first jaw member 110 and a second jaw member 120 pivotally engaged with one another. One or both of the first and second jaw members 110 and 120 is pivotable relative to the other between a spaced-apart position and an approximated position (see, e.g., FIG. 5 illustrating an approximated position, FIG. 7 illustrating a spaced-apart position, and FIG. 9 illustrating opening and closing direction). The first jaw member 110 includes a proximal cutting edge 501 facing away from the second jaw member 120 when the first and second jaw members 110 and 120 are in the approximated position. The second jaw member 120 includes a proximal flange 124 having first and second raised sidewalls 701 and 702 forming a proximal channel 703 (see, e.g., FIG. 7) therebetween. A distal end 704 of the proximal channel 703 is open. The proximal channel 703 receives the proximal cutting edge 501 of the first jaw member 110 therebetween in the approximated position. The proximal cutting edge 501 is exposed from the proximal channel 703 in the spaced-apart position.

The proximal cutting edge 501 includes a sharp tip or sharp edge and is employed in cutting treatment tissue (e.g., for removal of the treatment tissue). The sharp edge of the proximal cutting edge 501 may extend along an entire length of the proximal portion 510 of the first jaw member 110. The proximal cutting edge 501 may also receive electrosurgical energy for cutting treatment tissue (e.g., for removal of the treatment tissue).

In some aspects, a proximal portion 510 of the first jaw member 110 including the proximal cutting edge 501 has a height greater than a height of a distal portion 511 of the first jaw member 110. The proximal cutting edge 501 may have a sharp distal-facing end. The sharp distal-facing end may also be curved. The sharp distal-facing end of the proximal cutting edge 501 is also received in the proximal channel 703 when the first and second jaw members 110 and 120 are in the approximated position.

In some aspects, a pivot pin 601 is engaged with the first and second raised sidewalls 701 and 702 of the proximal flange 124 of the second jaw member 120 to pivotally engage the first and second jaw members 110 and 120 with one another. The first and second jaw members 110 and 120 each rotate about the pivot pin 601 to advance the proximal cutting edge 501 in and out of the proximal channel 703.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical forceps, comprising:
   an end effector assembly, including:
      a first jaw member and a second jaw member pivotally engaged with one another, at least one of the first or second jaw member pivotable relative to the other of the first or second jaw member between a spaced-apart position and an approximated position,
      the first jaw member including first and second surfaces on opposite sides thereof, the first surface disposed in opposition to the second jaw member and the second surface including a cutting edge disposed on a proximal portion thereof facing away from the second jaw member,
      the second jaw member including a proximal flange having first and second raised sidewalls defining a proximal channel therebetween, the proximal channel configured to:
         receive the cutting edge of the first jaw member therebetween when the first and second jaw members are disposed in the approximated position such that the cutting edge is disposed at or below a top surface of each of the first and second raised sidewalls; and
         expose the cutting edge of the first jaw member when the first and second jaw members are disposed in the spaced apart position.

2. The surgical forceps of claim 1, wherein the proximal portion of the first jaw member including the cutting edge includes a height greater than a height of a distal portion of the first jaw member.

3. The surgical forceps of claim 1, wherein a pivot pin is engaged with the first and second raised sidewalls of the proximal flange of the second jaw member to pivotally engage the first and second jaw members with one another.

4. The surgical forceps of claim 1, wherein a distal end of the proximal channel is open.

5. The surgical forceps of claim 1, wherein the cutting edge includes a sharp tip at a distal end thereof configured to cut tissue.

6. An end effector assembly, comprising:
   a first jaw member and a second jaw member pivotally engaged with one another, at least one of the first or second jaw member pivotable relative to the other of the first or second jaw member between a spaced-apart position and an approximated position;
   the first jaw member including first and second surfaces on opposite sides thereof, the first surface disposed in opposition to the second jaw member and the second surface including a cutting edge disposed on a proximal portion thereof facing away from the second jaw member; and the second jaw member including a proximal flange having first and second raised sidewalls defining a proximal channel therebetween, the proximal channel configured to:

receive the cutting edge of the first jaw member therebetween when the first and second jaw members are disposed in the approximated position such that the cutting edge is disposed at or below a top surface of each of the first and second raised sidewalls; and expose the cutting edge of the first jaw member when the first and second jaw members are disposed in the spaced apart position.

7. The end effector assembly of claim 6, wherein the proximal portion of the first jaw member including the cutting edge includes a height greater than a height of a distal portion of the first jaw member.

8. The end effector assembly of claim 6, wherein a pivot pin is engaged with the first and second raised sidewalls of the proximal flange of the second jaw member to pivotally engage the first and second jaw members with one another.

9. The end effector assembly of claim 6, wherein a distal end of the proximal channel is open.

10. The end effector assembly of claim 6, wherein the cutting edge includes a sharp tip at a distal end thereof configured to cut tissue.

* * * * *